United States Patent
Townsend et al.

(10) Patent No.: US 6,500,139 B1
(45) Date of Patent: Dec. 31, 2002

(54) ORTHOPEDIC KNEE BRACE JOINT ASSEMBLY HAVING A TRIGGER LOCKING MECHANISM

(75) Inventors: Jeffrey Townsend, Bakersfield, CA (US); Steven S. Knecht, Bakersfield, CA (US)

(73) Assignee: Townsend Design, Bakersfield, CA (US)

( * ) Notice: Subject to any disclaimer, the term of this patent is extended or adjusted under 35 U.S.C. 154(b) by 119 days.

(21) Appl. No.: 09/694,484

(22) Filed: Oct. 24, 2000

(51) Int. Cl.$^7$ .................................................. A61F 5/00
(52) U.S. Cl. .......................................... 602/26; 602/16
(58) Field of Search ................................ 602/5, 16, 26, 602/27; 16/324, 333, 334; 128/882

(56) References Cited

U.S. PATENT DOCUMENTS

| | | | |
|---|---|---|---|
| 4,428,369 A | | 1/1984 | Peckham et al. |
| 4,955,369 A | * | 9/1990 | Bledsoe ..................... 128/80 C |
| 5,259,832 A | | 11/1993 | Townsend et al. |
| 5,330,418 A | * | 7/1994 | Townsend .................... 602/26 |
| 5,356,370 A | | 10/1994 | Fleming |
| 5,409,449 A | | 4/1995 | Nebolon |
| 5,490,822 A | | 2/1996 | Biedermann |
| 5,921,946 A | | 7/1999 | Tillinghast et al. |

FOREIGN PATENT DOCUMENTS

| | | | |
|---|---|---|---|
| CH | 671876 | * | 10/1989 |
| WO | WO 02/58392 A1 | | 8/2001 |

* cited by examiner

*Primary Examiner*—Michael A. Brown
(74) *Attorney, Agent, or Firm*—Nixon Peabody LLP; David S. Safran

(57) ABSTRACT

A joint assembly for an orthopedic knee brace has a femoral bar, a tibial bar, a pair of upper side plates including a lateral side plate and a medial side plate, the pair of upper side plates being fixedly connected to the femoral bar; a pair of lower side plates including a lateral side plate and a medial side plate, the pair of lower side plates being fixedly connected to said tibial bar and further includes hook portions extending at a distal end of said pair of lower support plates. The joint assembly further includes a knee pad support configured for fitting on the knee joint of the wearer and a linkage mechanism for providing torsional strength to the joint assembly, the linkage mechanism including a first clevis formed by a lower rear area of said upper side plates, a second clevis formed by an upper rear area of the lower side plates, and an inner link interconnecting the upper side plates to the lower side plates to thereby interconnect the femoral link to the tibial link. Moreover, the joint assembly is further provided with a mechanism for releaseably locking the joint assembly in a substantially 180° position. The lock mechanism includes a release mechanism for slidingly placing the joint assembly in a lock or a release mode, and a pivotal trigger that effectively locks and releases the joint assembly while in the respective lock or release modes.

11 Claims, 5 Drawing Sheets

ORTHOPEDIC KNEE BRACE JOINT ASSEMBLY HAVING A TRIGGER LOCKING MECHANISM

BACKGROUND OF THE INVENTION

1. Field of the Invention

The present invention relates generally to orthopedic devices for the stabilization and control of a human knee joint that has been injured. More particularly, the invention relates to an orthopedic knee brace including a joint assembly having improved strength and stability characteristics and also an automatic lock mechanism which enables a wearer to releaseably lock the joint assembly in an effort to prevent the unintentional rotation of the joint assembly.

2. Description of the Related Art

Orthopedic knee braces are commonly worn by patients after surgery for treatment of an injury to the knee joint. Knee braces generally serve dual purposes: first, the brace stabilizes the joint in order to control its lateral movement. Second, they limit joint flexion and/or extension in an adjustable and controllable manner to prevent recurrence of injury to the knee. For example, an overall increase of injuries to the knee joint in professional and amateur athletics has given cause for the increased use of orthopedic knee braces to help facilitate the quick rehabilitation of the knee joint.

A knee brace of the initially mentioned type is disclosed in one of the present inventors U.S. Pat. No. 5,259,832, which discloses a multi-axis controlled knee brace utilizing a four bar joint mechanism including a femoral bar and a tibial bar, each of which has two pre-drilled holes for attachment of an inner lap-style link and an outer link that secure the tibial bar to the femoral bar. The joint of this brace, however, lacks a means to easily immobilize and subsequently release the joint. Furthermore, it has been found that a stronger joint is needed in cases where the joint undergoes torsional stress.

The use of orthopedic knee braces having locking members has become conventional within the prior art. Such an arrangement generally permit the wearer to releasably lock the hinge or joint of the knee brace in one or several angular positions to thereby restrict the degree of rotation of the brace. However, certain shortcomings have been encountered with regard to the use of the conventional locking members for orthopedic knee braces.

For example, U.S. Pat. No. 5,409,449 to Nebolon discloses an orthopedic knee brace having a rotatable hinge including two rotatably attached members and a detent mechanism for automatically and releasably locking the hinge in a fixed position of rotation. The detent mechanism includes an indentation formed in the attached end of one attached member and a block pivotally mounted on the other attached member. The block includes a locking projection that is biased toward the indentation and cooperates therewith to provide three positions of operation: a locked position, a release position, and an activated position. In the locked position, the locking projection fittingly engages the indentation, thereby substantially preventing rotation of the hinge. The release position displaces the locking projection a radial distance away from the indentation, thereby permitting the hinge to rotate freely. In the activated position, the block disengages the indentation and maintains an angular distance to enable automatic repositioning of the hinge assembly to the locked position whenever the locking projection and indentation angularly realign. While this design allows for the wearer to releasably lock the hinge, it does not provide for an effortlessness and simplistic locking and releasing of the knee joint since it requires cooperation between numerous parts to effectuate the locking and unlocking of the hinge.

Accordingly, there is still a need for a joint assembly for an orthopedic knee brace that provides improved strength and stability characteristics, especially when a lateral bending torque is applied to the joint assembly. There also is a need for a lock mechanism for use in an orthopedic knee brace that allows the wearer to manually and releasably lock the joint assembly in a simple and effective manner to prevent the accidental or unintentional rotation of the knee brace.

SUMMARY OF THE INVENTION

In view of the foregoing, it is an object of the present invention to provide a joint assembly for use with an orthopedic knee brace having enhanced strength characteristics as well as having the ability to provide enhanced kinematics to the wearer.

It is another object of the present invention to provide a lock mechanism for use with an orthopedic knee brace that can quickly and releasably lock the joint assembly to prevent the unintentional rotation of the knee brace.

These and other objects and characteristics of the present invention are achieved in accordance with a preferred embodiment, which provides a joint assembly for an orthopedic knee brace by which lateral side and medial side femoral links are pivotally connected to lateral side and medial side tibial links respectively, and also a lock mechanism having the ability to releasably lock the joint assembly of the knee brace in a quick and efficient manner. The lock mechanism is an advantageous feature since it prevents the unintentional rotation of the knee brace. Moreover, the joint assembly is advantageous since it provides greater flexibility and range of motion to the wearer.

An exemplary embodiment of the joint assembly generally exhibits the same kinematics as the four bar hinge described in the above-mentioned U.S. Pat. No. 5,259,832. The joint assembly comprises a femoral bar and a tibial bar, each having pre-drilled holes for attachment to upper and lower side plates. To provide for a sturdy design, both the femoral bar and tibial bar are in the form of upper struts and lower struts which can be formed of aluminum, titanium, or fiber and resin composites. A knee pad support comprising a generally circular shaped plastic condial attached to a condial link is configured to rest on the lateral and medial sides of the knee joint of the wearer for maintaining proper positioning of the joint assembly and for stabilizing the knee joint of the wearer. Moreover, a latch cap is fixedly connected to cap link to provide lateral protection to the joint assembly.

In an effort to enhance the strength and stability of the joint assembly, particularly when a lateral bending torque is applied thereto, an improved clevis-type joint is employed. The clevis-type joint includes a pair of outer linkages comprising a cap link, a condial link, and an inner link disposed between a pair of upper and lower side plates to fixedly attach the femoral bar to the tibial bar and thereby produce a glide and roll motion during extension and flexion of the wearer's leg.

The joint assembly is further provided with a mechanism for releaseably locking the joint mechanism in a substantially 180° position. The lock mechanism includes a release lever for slidingly placing the joint assembly in a lock or a release mode, and a pivotal trigger that effectively locks and releases the joint assembly while in either the lock or the release mode. The release lever is mounted for sliding movement between the lower side plates and has an elongated L-shaped body portion terminating into a tip portion at a distal end thereof, and at least two projecting pins perpendicularly extending from its body portion that are designed to slidingly move within laterally-placed groove portions of the lower side plates. The release lever further includes a handle portion designed to be engaged by a thumb or finger of the wearer to place the release mechanism into a first position in which the joint assembly is in a lock mode, and a second position in which the joint assembly is placed into a release mode.

The trigger is mounted for pivotal movement between the upper side plates and includes an elongated body portion, at least one projecting pin extending perpendicularly from the body portion and provides for the pivotal movement of the trigger, and also a hook portion located at a basal end of the trigger. The trigger also includes a handle portion designed to be engaged by the thumb or finger of the wearer to effectively lock and unlock the joint mechanism. The joint assembly is locked in a substantially 180° position by pivoting the trigger in a manner such that the hook portion of the trigger engages the hook portion on the lower side plates and tibial link. The joint assembly is unlocked by manipulating the handle portion of the trigger in a manner that disengages the hook portion of the trigger from the hook portions of the lower side plates and tibial link. Further, a biasing element, such as a coil spring, is disposed between a back surface end of the trigger and the femoral bar to bias the trigger into the respective lock and unlock positions.

The lock mechanism is provided with a unique safety feature that offers a wearer additional protection for cases in which the trigger is accidentally or intentionally unlatched while the joint assembly is in a locked mode. In such cases in which the release mechanism is maintained in the locked position, but the joint assembly is caused to rotate due to the unlatching of the trigger, the joint assembly will nonetheless automatically relock if the joint mechanism is rotated to a fully extended or substantially 180° position.

In operation, the joint assembly may be effortlessly and quickly unlocked by the wearer by sliding the release mechanism forward until the distal end of the release mechanism abuts the hook portion on the tibial link. Accordingly, because the distal end of the release mechanism abuts the hook portions of the tibial link, the hook portion of the trigger is prevented from interlocking with hook portions of the lower side plates and tibial link, thereby allowing the joint assembly to freely rotate.

These and other objects, features and advantages of the present invention will become more apparent from the following description when taken in conjunction with the detailed drawings which show, for purposes of illustration only, a single preferred embodiment of the present invention.

DETAILED DESCRIPTION OF THE PREFERRED EMBODIMENT

Figure 1:
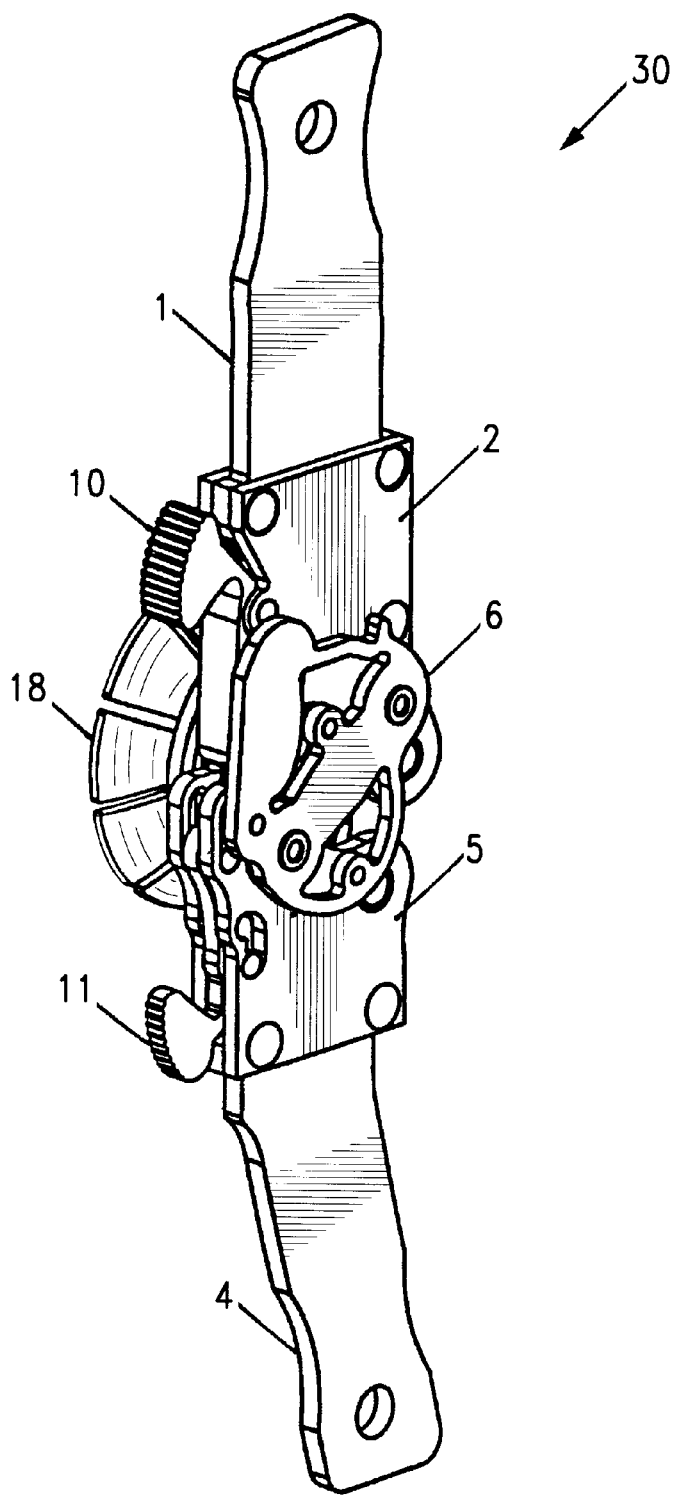
FIG. 1 is a perspective view of the joint assembly in accordance with a preferred embodiment of the invention.
Figure 2:
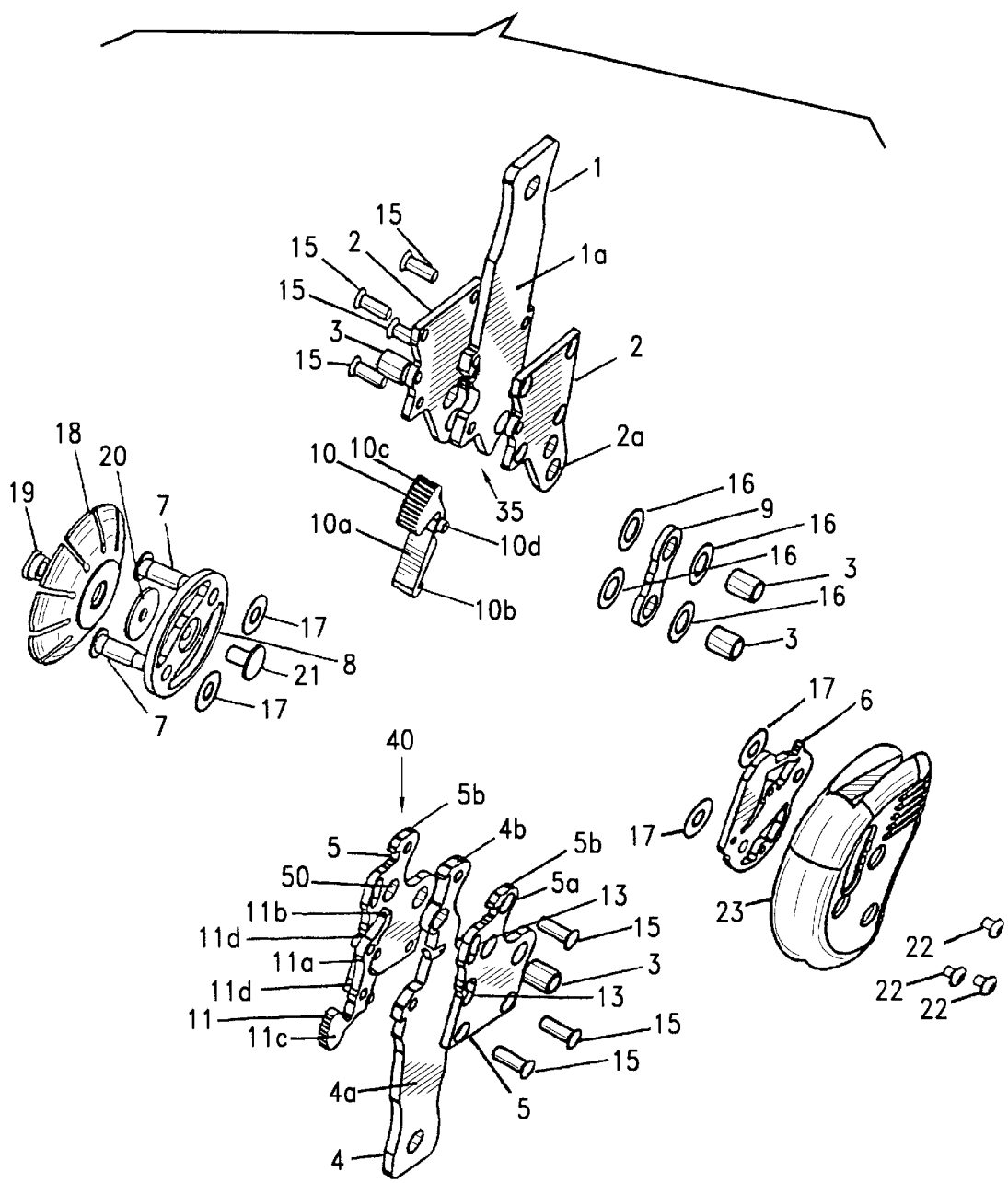
FIG. 2 is an exploded perspective view of the joint assembly including the lock mechanism in accordance with a preferred embodiment of the invention.

Referring to the drawings, joint assembly 30 of the present invention is best illustrated in FIGS. 1 and 2. The present invention employs a joint assembly 30 that generally exhibits the same kinematics as the four bar hinge previously described in U.S. Pat. No. 5,259,832. The joint assembly 30 includes femoral bar 1 and tibial bar 4, each having pre-drilled holes for attachment by sleeves 3 and rivets 15 to upper side plates 2 and lower side plates 5, respectively. Femoral bar 1 and tibial bar 4 are in the form of upper struts and lower struts and having body portions 1a, 4a which can be formed of aluminum, titanium, or fiber and resin composites. A knee pad support comprising a generally circular shaped plastic condial 18 having a circular array of radially directed flexible tabs is attached by rivets 7 to condial link 8, and is configured to rest comfortably on the lateral and medial sides of the knee joint of the wearer for stabilizing the knee joint of the wearer and for maintaining proper positioning of joint assembly 30. A latch cap 23 is fixedly connected by screws 22 to cap link 6 to provide lateral protection to the joint assembly 30.

A clevis-type joint is used to enhance the strength and stability of the joint assembly 30, particularly when a lateral bending torque is applied to joint assembly 30. The clevis-type joint includes a first clevis 35 formed by lower rear area of lower lateral (outer) and upper medial (inner) side plates 2, and a second clevis 40 formed by upper rear areas of upper lateral and lower medial side plates 5, between which an inner link 9 is pivotally connected by bushings 3 that are held by force-fit in openings 2a, 5a of the side plates 2, 5. Inner link 9 constitutes part of a four-bar linkage together with cap link 6 and condial link 8 which attach femoral bar 1 to tibial bar 4 to produce the same type of glide and roll motion during operation as previously described in U.S. Pat. No. 5,259,832. Attachment holes on upper side plates 2 and lower side plates 5 are preferably 23 mm apart, and those on inner linkage 9 are preferably 16 mm apart to provide for an approximately 8 mm posterior glide from 0 to 25 degrees of flexion, with the remaining motion being essentially a single pivot type of motion. Cap link 6 and condial link 8, preferably, are respectively fixedly attached to upper side plates 2 and lower side plates 5 through rivets 15. The invention is not limited to the use of the forms of attachment shown, and may foreseeably encompass alternative elements for fixedly attaching cap link 6, condial link 8 and inner link 9.

Joint assembly 30 further includes a trigger 10 mounted for pivotal movement between upper side plates 2. Trigger 10 includes an elongated body portion 10a located between upper side plates 2, a hook portion 10b located at a distal end of trigger 10, and a handle portion 10c located at a basal end thereof. The handle portion 10b is designed for engagement with a thumb or finger of the wearer to pivotally place trigger 10 in a first position which disengages hook portion 10b from hook portions 4b, 5b thereby releasing the lock, and a second position in which hook portion 10b of trigger 10 engages hook portions 4b, 5b of tibial bar 4 and lower side plates 5, thereby locking joint assembly 30. A coil spring 14 or the like is disposed between trigger 10 and femoral bar 1 to apply a force on the trigger 10 in a direction toward the second position. Trigger 10 also includes at least one projecting pin 10d perpendicularly extending from the body portion 10a for providing pivotal movement of trigger 10 in the respective first and second positions.

Figure 3:
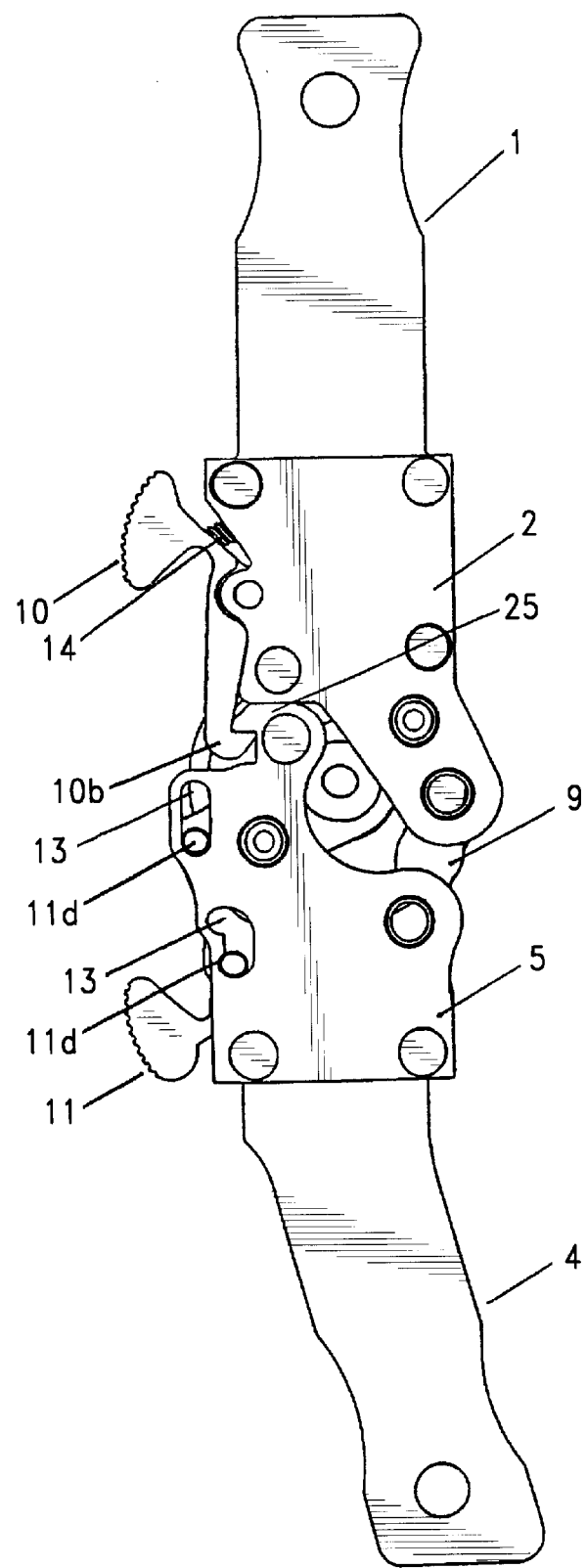
FIG. 3 is a side view of the lock mechanism in a locked position in accordance with a preferred embodiment of the invention, with the outer cap link removed.

The joint assembly 30 is also provided with a release lever 11 that is mounted for sliding movement between lower side plates 5 at a tibial end of joint assembly 30. Release lever 11 has an elongated L-shaped body portion 11a located between lower side plates 5, a front end portion 11b and a handle portion 11c designed for engagement with a thumb or finger of the wearer to pivotally place the brace into a first or disengaged position that enabling locking of joint assembly 30 and a second or blocking position that precludes locking of joint assembly 30. As illustrated in FIG. 3, release lever 11 also includes front and rear projecting pins 11d perpendicularly extending from the side of body portion 11a that provides for gliding movement of release lever 11 within groove portions 13 of lower side plates 5 between the disengaged position enabling locking of the joint assembly 30 and the blocking position precluding locking of the joint assembly 30. Furthermore, the shape of the front end of body portion 11a, having a sloping cam surface 11b which is engageable with a sloping front face of hook portion 10b, coupled with the path of its movement, enable release lever 11 to disengage hook portion 10b from hook portions 4b, 5b when the release lever 11 is moved from a disengaged position (FIG. 3) to a blocking position (FIG.4).

Figure 5:
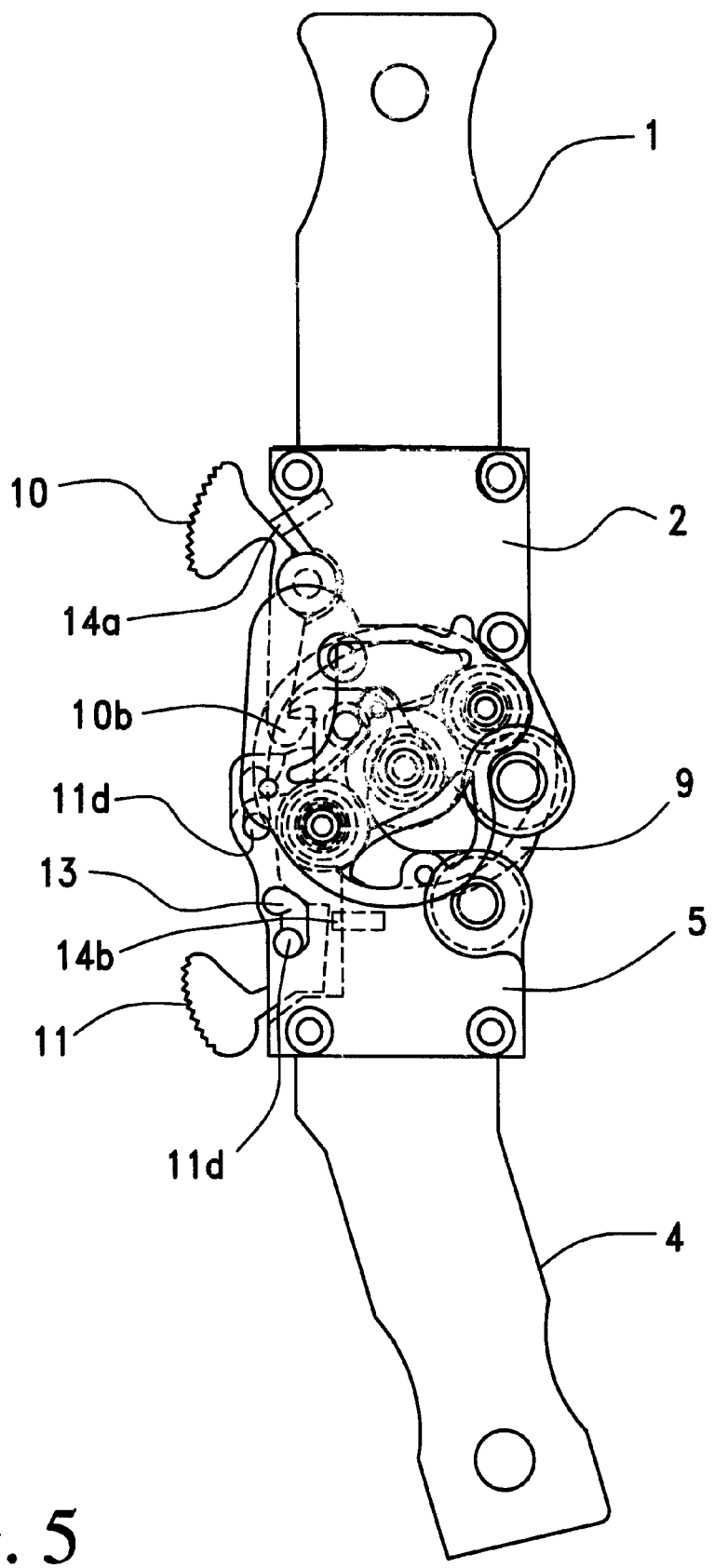
FIG. 5 is a view of the lock mechanism corresponding to that of FIG. 3, but with the lateral side plates also removed.

FIGS. 3 and 5 show a side view of the locking mechanism without the outer cap link 6 attached thereto, in a locked position in accordance with a preferred embodiment of the invention. In the locked position, forward (upper) and rear (lower) pin projections 11d of release lever 11 lie in the rear (bottom) end of groove portions 13 contained in lower side plates 5. In addition, while in the locked position, trigger 10 is positioned in a manner such that the hook portion 10b is placed in an interlocking engagement with hook portions 4b, 5b on lower side plates 5, thereby preventing rotation of joint assembly 30. Coil spring 14a is shown in an extended position between femoral link 1 and trigger element 10, causing trigger element 10 to pivot towards the locked position. As illustrated in FIG. 5, coil spring 14b is placed in a compressed position when rear (lower) pin projection 11d sits in the lower end of its respective groove portion 13. However, when joint assembly 30 is placed into an unlocked position coil spring 14b is placed in an extended position to urge rear (lower) pin projection 11d to sit in the upper end of its respective groove portion 13 so that sloping cam surface 11b engages a sloping front face of hook portion 10b.

Figure 4:
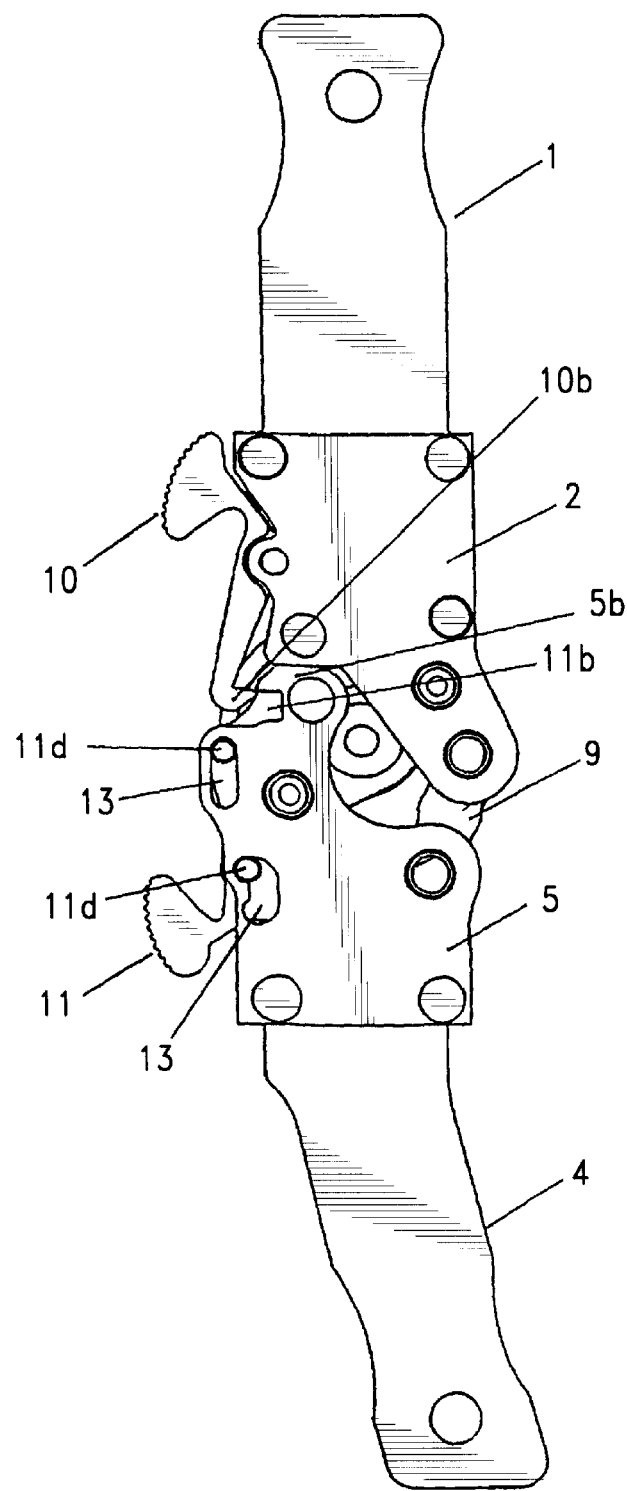
FIG. 4 is a side view of the lock mechanism in an unlocked position in accordance with a preferred embodiment of the invention, with the outer cap link removed.

FIG. 4 best illustrates the lock mechanism in a locked position in accordance with a preferred embodiment of the invention. Accordingly, while in the locked position, forward (upper) and rear (lower) pin projections 11d of release lever 11 lie in the upper end of groove portions 13 contained in lower side plates 5. In addition, while in the locked position, trigger 10 is positioned in a manner such that hook portion 10b is placed in an interlocking engagement with hook portions 4b, 5b created by tibial link 4 and lower side plates 5, thereby preventing the rotation of joint assembly 30. Coil spring 14a is in an extended position between femoral link 1 and trigger element 10, thereby holding rigger element 10 pivoted into the locked position.

Moreover, the lock assembly 30 is provided with a unique safety feature that offers a wearer added protection for instances in which trigger 10 is accidentally or intentionally unlatched while joint assembly 30 is in a locked mode. In cases in which release mechanism 11 is maintained in the locked position but joint assembly 30 is caused to rotate due to the trigger 10 being unlatched, the joint assembly 30 will automatically relock if the joint assembly 30 is rotated to the fully extended or substantially 180° position.

Referring again to FIGS. 3, 4 and 5, during operation, the joint assembly 30 may be effortlessly and quickly unlocked manually by sliding release lever 11 upward until the cam surface 11b on the distal end of release lever 11 abuts hook portion 10b, forcing it out of engagement with hook portions 4b, 5b. Further, because the cam surface 11b of release lever 11 its flush across the open end of hook portion 4b (FIG. 4), the hook portion 10b is prevented from re-locking with hook portions 4b, 5b, thereby allowing the joint assembly 30 to freely rotate back and forth during extension and flexion of the wearer's leg until such time the release lever is moved to its locked position.

While the present invention has been illustrated and described in connection with what is considered the most practical and preferred embodiment, it is understood that this invention is not limited to the embodiment disclosed herein but is intended to cover various arrangements included within the spirit and scope of the broadest interpretations and equivalent arrangements.

What is claimed is:

1. A joint assembly for an orthopedic knee brace for controlling the rotational movement of the femur relative to the tibia during extension and flexion of a wearer's leg, said joint assembly comprising:

a femoral bar;

a tibial bar;

a pair of upper side plates including an upper lateral side plate and an upper medial side plate, said pair of upper side plates being fixedly attached to said femoral bar;

a pair of lower side plates including a lower lateral side plate and a lower medial side plate, said pair of lower side plates being fixedly attached to said tibial bar;

a linkage mechanism pivotally connecting said upper side plates with said lower side plates for enabling flexion and extension of a wearer's leg; and a lock mechanism for releasably locking said joint assembly for fixing said joint in an extended position, said lock mechanism including:

a catch arrangement provided in one of said pairs of side plates;

a trigger pivotally mounted to the other of said pairs of side plates, said trigger being movable between a locking position engaging said catch arrangement and locking said joint assembly, and a release position out of engagement with said catch arrangement allowing movement of said joint assembly; and a release lever mounted for movement between a disengaged position permitting locking engagement of said trigger with said catch arrangement and a blocking position preventing locking engagement of said trigger with said catch arrangement.

2. A joint assembly as recited in claim 1, wherein said trigger includes a body portion, a handle portion located at a basal end of said body portion, a hook portion located at a distal end of said body portion, and at least one projecting pin perpendicularly extending from said body portion, said at least one projecting pin pivotally connecting said trigger to said upper pair of side plates.

3. A joint assembly as recited in claim 2, wherein said catch arrangement comprises a hook portion on said tibial bar and hook portions on said lower side plates; and wherein said hook portion of said trigger engages said hook portion of said tibial bar and said hook portions on said lower side plates in said locking position.

4. A joint assembly as recited in claim 1, wherein said release lever includes a body portion, an end portion located at a distal end of said body portion, a handle portion located at a basal end of said body portion, an upper projecting pin and a lower projecting pin perpendicularly extending from said body portion and adapted for movement within groove portions provided in said lower side plates, said upper projecting pin and said lower projecting pin enabling movement of said release lever between said disengaged position and said blocking position.

5. A joint assembly as recited in claim 1, wherein said linkage mechanism includes a first clevis formed by a lower rear area of said upper side plates, a second clevis formed by an upper rear area of said lower side plates, an inner link interconnecting said upper side plates to said lower side plates, and an outer medial link interconnecting said upper medial side plate to said lower medial side plate, and an outer lateral link interconnecting said upper lateral side plate to said lower lateral side plate.

6. A joint assembly as recited in claim 1, further comprising means for biasing said trigger element in a direction from said release position toward said locking position.

7. A joint assembly as recited in claim 1, wherein said trigger is pivotally mounted between said pair of lower side plates and said release lever is mounted for sliding movement between said upper side plates.

8. A joint assembly as recited in claim 7, wherein said trigger includes a body portion, a handle portion located at a basal end of said body portion, a hook portion located at a distal end of said body portion, and at least one projecting pin perpendicularly extending from said body portion, said at least one projecting pin pivotally connecting said trigger to said upper pair of side plates.

9. A joint assembly as recited in claim 1, wherein said joint assembly comprises a four-bar joint assembly.

10. A joint assembly for an orthopedic knee brace for controlling the rotational movement of the femur relative to the tibia during extension and flexion of a wearer's leg, said joint assembly comprising:
   a femoral bar;
   a tibial bar;
   a pair of upper side plates including an upper lateral side plate and an upper medial side plate, said pair of upper side plates being fixedly attached to said femoral bar;
   a pair of lower side plates including a lower lateral side plate and a lower medial side plate, said pair of lower side plates being fixedly attached to said tibial bar and; and
   a linkage mechanism for providing rotation to said joint assembly during extension and flexion of the wearer's leg, said linkage mechanism including:
     a first clevis formed by a lower rear area of said upper side plates;
     a second clevis formed by an upper rear area of said lower side plates;
     an inner link interconnecting said upper side plates to said lower side plates;
     an outer medial link interconnecting said upper medial side plate to said lower medial side plate; and
   an outer lateral link interconnecting said upper lateral side plate to said lower lateral side plate.

11. A joint assembly as recited in claim 10, wherein said joint assembly comprises a four-bar joint assembly.

* * * * *